United States Patent [19]

Higashide et al.

[11] 4,245,047

[45] Jan. 13, 1981

[54] ANTIBIOTICS PRODUCED FROM THE MICROORGANISM NOCARDIA

[75] Inventors: Eiji Higashide, Takarazuka; Mitsuko Asai, Osaka; Toru Hasegawa, Kawanishi, all of Japan

[73] Assignee: Takeda Chemical Industries, Ltd., Osaka, Japan

[21] Appl. No.: 66,823

[22] Filed: Aug. 14, 1979

Related U.S. Application Data

[62] Division of Ser. No. 815,050, Jul. 12, 1977, Pat. No. 4,187,292.

[30] Foreign Application Priority Data

Apr. 1, 1977 [JP] Japan .................................. 52/37884
Mar. 31, 1977 [JP] Japan .................................. 52/37168

[51] Int. Cl.$^3$ ........................ C12P 13/00; C12P 17/10

[52] U.S. Cl. .................................... 435/128; 435/121; 435/170; 435/872

[58] Field of Search ................ 435/128, 170, 872, 121

[56] References Cited

U.S. PATENT DOCUMENTS 2,951,790  9/1960  Stainbrook ........................... 424/123

*Primary Examiner*—Lionel M. Shapiro
*Attorney, Agent, or Firm*—Wenderoth, Lind & Ponack

[57] ABSTRACT

The present invention relates to a method of producing the antibiotics C-14919 E-1 and/or E-2 by cultivating an antibiotic C-14919 E-1 and/or E-2 producing strain of the genus Nocardia in a culture medium and accumulating said antibiotics. These antibiotics have a wide range of antibiotic activity and they are useful as germicides or disinfectants.

2 Claims, 2 Drawing Figures

ANTIBIOTICS PRODUCED FROM THE MICROORGANISM NOCARDIA

This is a division, of application Ser. No. 815,050, filed July 12, 1977, now U.S. Pat. No. 4,187,292, issued Feb. 5, 1980.

This invention relates to novel Antibiotics C-14919 E-1 and E-2, and a method of producing the same.

We collected many soil and other samples and performed a screening research for antibiotics on the microorganisms isolated from such samples. The research shed light on the fact that certain of those microorganisms were able to produce novel antibiotic agents, the fact that such microorganisms belonged to the genus Nocardia and the fact that by cultivating any of those microorganisms in a suitable nutrient medium, it was possible to have said antibiotic accumulated in the cultured broth. The above novel antibiotic were designated as Antibiotics C-14919 E-1 and E-2, respectively. The above findings provided impetus for a further research which has resulted in the development of this invention.

This invention is, therefore, concerned with:

(1) Antibiotic C-14919 E-1 and Antibiotic C-14919 E-2; and (2) A method of producing Antibiotic C-14919 E-1 and/or E-2 characterized in that said method comprises cultivating an Antibiotic C-14919 E-1 and/or E-2-producing strain of the genus Nocardia in a culture medium to cause said strain to elaborate and accumulate Antibiotic C-14919 E-1 and/or E-2 in the resultant broth and harvesting said Antibiotic C-14919 E-1 and/or E-2 from the broth.

Throughout this specification, Antibiotic C-14919 E-1 and Antibiotic C-14919 E-2 will sometimes be referred to briefly as C-14919 E-1 and C-14919 E-2, respectively.

The new Antibiotic C-14919 E-1 and/or E-2-producing microorganism which is employed herein according to this invention may be any strain belonging to the genus Nocardia which is able to elaborate and to accumulate the Antibiotic C-14919 E-1 and/or E-2.

The microorganism, which we have isolated, is one of the preferred microorganisms which can be employed according to this invention.

The aforementioned microorganism is actinomycete Strain No. C-14919 (hereinafter sometimes referred to briefly as Strain No. C-14919) which is an actinomycete organism discovered in the course of our screening for antibiotic producers and which is a novel type of microorganism of the genus Nocardia as will be seen from the following description.

(A) Microbiological Characteristics of Strain No. C-14919

The microbiological characters of Strain No. C-14919 were investigated by procedures analogous with those proposed by Schirling & Gottlieb [International Journal of Systematic Bacteriology 16, 313-340 (1966)]. The results of cultivation at 28° C. over 21 days are as follows;

(1) Morphological characters

The vegetative mycelium extends far, developing into branches, both on agar and in liquid media. Many of the hyphae measure 0.8 to 1.2 μm in diameter and the hyphae are fragmented depending on cultural conditions.

The strain gives good growth on various taxonomical media, with the aerial mycelium superimposed on the vegetative mycelium, although it forms coremia like bodies (50–200 μm × 200–1500 μm) on which the aerial growth takes place. Many of the aerial mycelia are flexuous or straight, with a loosely spiral like configuration being found on a few occasions. Microscopic examination of aged cultures reveals that only in few cases the conidia like form occur in chains, while the cell suspensions obtained from the surfaces of such cultures, as viewed under a microscope, contains elongated ellipsoidal (0.8–1.2 × 3.7–6.7 μm) and ellipsoidal (0.8–1.2 × 1.0–2.0 μm) bodies resembling conidia.

Electron-microscopic examinations showed that these bodies had smooth surfaces.

(2) The constituents of the cell

The strain was inoculated into a modified ISP No. 1 medium and cultured at 28° C. for 66 to 90 hours under shaking culture, at the end of which time the cells were collected and rinsed. By the method of B. Becker et al. [Applied Microbiology 12, 421 (1964)] and the method of M. P. Lechevalier et al. [Journal of Laboratory and Clinical Medicine 71, 934(1968)], the above cells were examined for diaminopimelic acid and sugar composition. The former was found to be the meso-form, while spots were in evidence which corresponded to galactose and arabinose.

(3) Characteristics on taxonomical media

The strain gives comparatively good growth on various media, with the vegetative mycelium being colorless to pale yellow in initial phases of culture and light yellowish tan to yellowish tan in later phases. Moreover, substantially no soluble pigments were produced in the taxonomical media used for the present strain. The aerial mycelium is powdery and grows moderately, being white to yellow or light yellowish tan.

The characteristics of the strain in various taxonomical media are set forth in Table 1.

TABLE 1

Cultural characteristics of Strain No. C-14919 on taxonomical media

| | | |
|---|---|---|
| (A) | Sucrose nitrate agar | |
| | Growth(G): | Poor, colorless to light yellow |
| | Aerial mycelium(AM): | None |
| | Soluble pigment(SP): | None |
| (B) | Glycerol nitrate agar | |
| | G: | Poor, colorless to light yellow; coremia like bodies formed. |
| | AM: | Scant, Lt Ivory (2ca)* |
| | SP: | None |
| (C) | Glucose asparagine agar | |
| | G: | Moderate, colorless to Brite Yellow (3na)*; coremia like bodies formed. |
| | AM: | Scant, white to Lt Ivory (2ca)* |
| | SP: | None |
| (D) | Glycerol aspargine agar | |
| | G: | Moderate, white to light orange yellow; coremia like bodies formed. |
| | AM: | Scant, Lt Ivory (2ca)* |
| | SP: | None |
| (E) | Starch agar | |
| | G: | Moderate, Lt Ivory (2ca)* to Lt Wheat (2ea)*; coremia like bodies formed |
| | AM: | Abundant, Lt Ivory (2ca)* |
| | SP: | None |
| (F) | Nutrient agar | |
| | G: | Moderate, Colonial Yellow (2ga)* to Brite Maize (31a)*; coremia like bodies formed |

TABLE 1-continued

Cultural characteristics of Strain No. C-14919 on taxonomical media

|   |   |   |
|---|---|---|
|   | AM: | Moderate, white to Pearl Pink (3ca)* |
|   | SP: | None |
| (G) | Calcium malate agar | |
|   | G: | Moderate, light yellow to Colonial Yellows (2ga)*; coremia like bodies formed |
|   | AM: | Moderate, light yellow to yellow |
|   | SP: | None |
|   | Other character: Calcium solubilize | |
| (H) | Yeast extract-malt extract agar | |
|   | G: | Moderate, Amber (3nc)*; coremia like bodies formed |
|   | AM: | Moderate, white |
|   | SP: | None |
| (I) | Oatmeal agar | |
|   | G: | Moderate, Amber (3nc)* to Brite Yellow (3na)*; coremia like bodies formed |
|   | AM: | Moderate, light yellow |
|   | SP: | None |
| (J) | Tyrosine agar | |
|   | G: | Moderate, Amber (3lc)*; coremia like bodies formed |
|   | AM: | Scant, light yellow |
|   | SP: | None |
| (K) | Potato plug | |
|   | G: | Moderate, Lt Amber (3ic)*; coremia like bodies formed |
|   | AM: | None |
|   | SP: | The plug becomes pale yellowish tan |
| (L) | Peptone yeast extract iron agar | |
|   | G: | Moderate, light yellowith tan to light orange yellow |
|   | AM: | None |
|   | SP: | None |

*The color codes according to Color Harmony Manual, 4th ed. (Container Corporation of America, 1958).

(4) Physiological characters

Physiological characters of the strain are shown in Table 2. Temperature range for growth: 12° C. to 38° C. The temperature range in which good aerial mycelium growth occurs on agar (ISP No. 2) is 20° to 32° C.

TABLE 2

The physiological characters of Strain No. C-14919

| | |
|---|---|
| Temperature range for growth: | 12° C.–38° C. |
| Temperature range for sporulation: | 20° C.–28° C. |
| Liquefaction of gelatin: | Positive |
| Hydrolysis of starch: | Positive |
| Reduction of nitrates: | Positive |
| Peptonization of milk: | Positive |
| Coagulation of milk: | Doubtful positive |
| Decomposition of casein: | Positive |
| Production of melanoid pigments: Negative (peptone yeast extract iron agar), negative (tyrosine agar) | |
| Decomposition of tyrosine: | Positive |
| Decomposition of xanthine: | Negative |
| Decomposition of hypoxanthine: | Negative |
| Tolerance to lysozyme: | Positive |
| Tolerance to sodium chloride: | 2% |

(5) Utilization of various carbon sources

The utilization of various carbon sources was investigated using a medium described in Pridham and Gottlieb [Journal of Bacteriology 56, 107(1948)]. The resultant spectrum is shown in Table 3.

TABLE 3

The utilization of carbon sources by Strain No. C-14919

| Source of carbon | Growth | Source of carbon | Growth |
|---|---|---|---|
| D-Xylose | + | Raffinose | ± |
| L-Arabinose | − | Melibiose | + |
| D-Glucose | ++ | i-Inositol | − |
| D-Galactose | ++ | D-Sorbitol | − |
| D-Fructose | +++ | D-Mannitol | + |
| L-Rhamnose | ± | Glycerol | + |
| D-Mannose | + | Soluble starch | + |
| Sucrose | ++ | Control | − |
| Lactose | ± | | |
| Maltose | ± | | |
| Trehalose | + | | |

Note:
+++: Luxuriant growth
++: Good growth
+: Growth
±: Poor growth
−: No growth

(6) Other characteristics

The cells were harvested by the procedure previously described in 2) and DNA was prepared by a procedure analogous to that of J. Murmar et al. [Journal of Molecular Biology, Vol. 3, 208, 1961]. The G-C content of the DNA was found to be about 71 mole %.

Gram-staining of the vegetative mycelium of this strain produced a positive reaction.

The above characteristics of strain No. C-14919 were compared with the descriptions in S. A. Waksman's "The Actinomycetes Vol. 2" [The Williams and Wilkins Co., 1961]; R. E. Buchanan and N. E. Gibbons, "Bergey's Manual of Determinative Bacteriology, 8th ed.", 1974; and other literatures. While this strain was thought to belong to Group III of the genus Nocardia, failure to find any species having the characters so far described among the known species led us to conclude that it was a novel species of microorganisms.

The present Strain No. C-14919 has been deposited at Fermentation Research Institute, Agency of Industrial Science and Technology (FERM) under the receipt number of 3991; at Institute for Fermentation, Osaka (IFO) under the accession number of IFO 13723, and at The American Type Culture Collection (ATCC), Maryland, U.S.A. under the accession number of ATCC 31280.

While Strain No. C-14919 is a novel species of the genus Nocardia as just mentioned, it is liable, as are microorganisms generally, to undergo variations and mutations, either spontaneously or under the influence of a mutagen. For example, the many variants of the strain which are obtainable by irradiation of the parent with X-rays, gamma rays, and ultraviolet light, etc., by monocell isolation, by cultivation on media containing various chemicals, or by other mutagenic treatments, as well as the mutants spontaneously obtained from the parent strain, may not be substantially considered to represent any other distinct species but, rather, any of such variants and mutants which is still able to elaborate C-14919 E-1 and/or E-2 may be invariably utilized for the purposes of this invention. By way of example, subjecting Strain No. C-14919 to various mutagenic treatments yields mutants which produce soluble pigments from light yellow to light yellowish tan or tan, mutants whose substrate mycelia are colorless or yellowish green, or orange red, mutants which produce abundant white mycelia or no mycelium at all, or mutants whose hyphae are liable to fragmentation.

The culture medium employed in the practice of this invention may be whichever of a liquid or a solid medium, only if it contains nutrients which the strain may utilize, although a liquid medium is preferred for high-production runs. The medium may contain carbon and nitrogen sources which Strain No. C-14919 may assimilate and digest, inorganic matter, trace nutrients, etc. As examples of said carbon sources may be mentioned glucose, lactose, sucrose, maltose, dextrin, starch, glycerol, mannitol, sorbitol, and fats and oils (e.g. soybean oil, lard oil, chicken oil, etc.). The nitrogen sources may for example be meat extract, yeast extract, dried yeast, soybean meal, corn steep liquor, peptone, cottonseed flour, spent molasses, urea, ammonium salt (e.g. ammonium sulfate, ammonium chloride, ammonium nitrate, ammonium acetate, etc.) and so forth. The medium may further contain salts of sodium, potassium, calcium, magnesium, etc., metal salts of iron, manganese, zinc, cobalt, nickel, etc., and organic acid salts such as acetates and propionates. Further, the medium may contain, as added, various amino acids (e.g. glutamic acid, aspartic acid, alanine, lysine, methionine, proline, etc.), peptides (e.g. dipeptides, tripeptides, etc.), vitamins (e.g. $B_1$, $B_2$, nicotinic acid, $B_{12}$, C, etc.), nucleic acids (e.g. purine, pyrimidine and the corresponding derivatives) and so forth. For the purpose of adjusting the pH of the medium, there may be added an inorganic or organic acid, alkali, buffer or the like. Suitable amounts of oils and fats, surfactants, etc. may also be added as antiforms.

The cultivation may be conducted by any of the stationary, shake, aerobic submerged and other cultural methods. For high production runs, submerged aerobic culture is of course preferred. While the conditions of culture, of course, depends on the condition and composition of the medium, the strain used, cultural method and other factors, it is normally preferred to carry out incubation at 20° to 32° C. with an initial pH near neutrl. Particularly desirable is a temperature from 23° to 26° C. in an intermediate stage of cultivation, with an initial pH of 6.0 to 7.0. While the incubation time also is variable according to said factors, it is advisable to continue the incubation until the titer of the desired antibiotic elaboration product is maximal. In the case of shake culture or aerobic submerged culture in fluid medium, the time required normally ranges from about 72 to 192 hours.

The pH suited for the production of the antibiotics is near neutral, the optimum range being pH 6.5 to pH 7.0. The yield can be increased by controlling the medium pH in the course of cultivation, by the addition of an acid or alkali or by selecting the proper medium composition. Thus, the yield of the antibiotics increases considerably as medium ingredients, inorganic phosphates are added in an amount more than necessary for growth of the strain. i.e. 1000 to 7000 ppm., or certain assimilable carbohydrates which are ready to form acids, e.g. glucose, mannitol, etc., are employed as sources of carbon, together with suitably selected sources of nitrogen.

Antibiotics C-14919 E-1 and E-2, tus elaborated by the present strain, normally occur extracellularly but there are cases in which the cells contain about 10 to 30 percent of the total yields of the antibiotics. The potency titration of the antibiotic agents can be accomplished by the cylinder method or the paper disk method, which employs *Candida albicans* IFO 0583 as an assay organism and TSA (Trypticase soy agar, BBL) as an assay medium.

The antibiotics occur in both the filtrate and cells which may be obtained from the cultured broth. Thus, the broth is filtered or centrifuged to recover the cells and the filtrate or supernatant independently. The potency of the filtrate is assayed directly and that of the cells is assayed after they are stirred with the same volume of 70% acetone-water as the filtrate at 20° C. for one hour. The assay method is the one described hereinbefore, the assay organism being *Candida albicans*.

Because C-14919 E-1 and E-2, which are produced in the fermentation broth, are lipophyl and neutral substances, they can be conveniently recovered by separation and purification procedures which are normally employed for the harvest of such microbial metabolites. For example, there may be employed a procedure which utilizes the difference in solubility between the antibiotic and impurity, a means which utilizes the difference in adsorptive affinity between the antibiotic and impurity of various adsorbents such as activated carbon, macroporous non-ionic resins, silica gel, alumina, etc., a procedure of removing the impurities by means of ion exchange resins and so forth. These procedures may be used singly, in a suitable combination or applied in repetition. Since, as aforementioned, C-14919 E-1 and E-2 occur in both the filtrate and cells, whichever of the following procedures may be adopted. (1) The culture broth as such, before separation of the cells, is extracted with a solvent or (2) the cells and the filtrate or supernatant as obtained by filtration or centrifugation are independently extracted with solvents.

Where the cells and filtrate are independently extracted, the following procedure may be followed with advantage. As the solvents suited for extraction from the filtrate, there may be mentioned organic solvents immiscible with water, such as fatty acid esters, e.g. ethyl acetate, amyl acetate, etc.; alcohols, e.g. butanol; halogenated hydrocarbons, e.g. chloroform; and ketones, e.g. methyl isobutyl ketone. The extraction is carried out in the neighborhood of neutrality and, preferably, is accomplished with ethyl acetate from the broth preadjusted to pH 7. After the extract is washed with water and concentrated, C-14919 E-2 is obtained as crude crystals. The filtrate remaining after separation of said crude crystals is rich in E-1.

The extraction from the cells may be accomplished using a mixture of water with a water-miscible organic solvent, such as a mixture of water with a lower alcohol (e.g. methanol, ethanol, etc.) or a mixture of water with a ketone (e.g. acetone, methyl ethyl ketone, etc.); or by means of a water-immiscible organic solvent such as a halogenated hydrocarbon (e.g. methylene dichloride). It is, however, advantageous to employ 70% acetone-water. Thus, the cells are reconstituted with the same volume of 70% acetone-water as the corresponding filtrate, and the mixture is stirred at room temperature for 3 hours. By this procedure, all the C-14919 E-1 and E-2 occurring in the cells are extracted.

The solvent extracts are pooled and the solvent, e.g. acetone, is removed under reduced pressure. The aqueous solution is extracted with ethyl acetate as in the case of the filtrate and the solvent layer is washed with water and concentrated under reduced pressure. To the concentrate is added hexane or the like to precipitate the active components. A mixture of C-14919 E-1 and E-2 can thus be obtained by centrifugation or filtration. Separation of the mixture into components may be accomplished by adsorption chromatography on various adsorbents. For this purpose, various carriers commonly used for adsorption of antibiotic substances can be employed. For example, adsorbent resins, silica gel, alumina, etc. may be mentioned. For eluting the antibiotics from such adsorbent resins, use is made of a mixture of water and a water-miscible organic solvent such as a lower alcohol or lower ketone. As said lower alcohol may be mentioned methanol, ethanol, propanol, butanol, etc. and said lower ketone may for example be acetone, methyl ethyl ketone. Esters such as ethyl acetate may also be employed. A typical procedure may be as follows. The crude is dissolved in 40% methanol-water and adsorbed on a column of Diaion HP-10 (Mitsubishi Kasei). The column is first washed with 40% methanol-water and, then, elution is carried out with 60% methanol-water, whereby the C-14919 E-2 fraction is obtained. Elution with 90% methanol-water yields the C-14919 E-1 fraction. Each fraction is concentrated under reduced pressure and, after addition of methanol, allowed to stand. The procedure yields crystals of C-14919 E-1 and crystals of C-14919 E-2 from the corresponding fractions. Where silica gel is used as said absorbent, development can be started using a nonpolar solvent with the addition of a polar solvent, e.g. methanol, in small increments, whereby C-14919 E-1 and E-2 are eluted. The crystals of C-14919 E-1 are recrystallized from ethyl acetate, methanol, aqueous methanol or the like, and the C-14919 E-2 may also be recrystallized from similar solvents.

C-14919 E-1 and E-2, which can thus be obtained, are convertible to each other by reversible oxidation-reduction. Thus, whilst reduction of C-14919 E-1 with a reducing agent, e.g. a hydrosulfite, yields C-14919 E-2, oxidation of C-14919 E-2 with an oxidizing agent such as ferric chloride yields C-14919 E-1.

The physical and chemical properties of the novel antibiotics C-14919 E-1 and E-2 crystals obtained in the above manner are as follows (Table 4).

TABLE 4

|   |   | C-14919 E-1 | C-14919 E-2 |
|---|---|---|---|
| (1) | m.p. | 187° C. (decomp.) | 148° C. (decomp.) |
| (2) | Appearance | yellow crystals (needles or prisms) | pale yellow crystals (needles or prisms) |
| (3) | Solubility | Insoluble in: petroleum ether, hexane, water<br>Sparingly soluble in: diethyl ether, benzene<br>Soluble in: ethyl acetate, chloroform, butanol, methyl isobutyl ketone, ethanol, acetone, methanol<br>Readily soluble in: dimethylsulfoxide | Insoluble in: petroleum ether, hexane<br>Sparingly soluble in: diethyl ether, benzene, water, chloroform<br>Soluble in: ethyl acetate, butanol, methyl isobutyl-ketone, ethanol, acetone, methanol<br>Readily in: dimethylsulfoxide |
| (4) | Acid, neutral or basic | a neutral substance | a neutral substance |
| (5) | Elemental analysis % | C 65.31, 65.05, 64.85<br>H 7.71, 7.58, 7.62<br>N 5.01, 5.01<br>O 21.37, 22.83, 22.45 | C 62.32, 62.07<br>H 8.58, 8.43<br>N 4.82, 4.78<br>O 20.81, 20.81 |
| (6) | Empirical formula | $C_{30-32}H_{42-48}N_2O_{8-9}$ | $C_{30-32}H_{44-50}N_2O_{8-9} \cdot xH_2O$ |
| (7) | Ultraviolet absorption spectrum<br>MeOH . N—HCl(9:1) (nm) ($E_{1cm}^{1\%}$) $\lambda_{max}$<br>MeOH$_{(nm)(E_{1cm}^{1\%})}$ $\lambda_{max}$<br>MeOH . N—NaOH(9:1)(nm)($E_{1cm}^{1\%}$) $\lambda_{max}$ | 274(455),240(sh), 397(43)<br>274(455),240(sh), 397(43)<br>236(585),265(500), 550(56) | 255(295) 308(sh)<br>255(290) 308(sh)<br>236(505),265(420) 550(50) |
| (8) | Infrared absorption spectrum (KBr) | See FIG. 1<br>Dominant peaks (cm$^{-1}$)<br>3430,3340,2950, 2910,1740,1692, 1660,1645,1605, 1500,1375,1315, 1120,1100,1085 1060,1025 | See FIG. 2<br>Dominant peaks (cm$^{-1}$)<br>3480,3250,2980, 1685,1625,1598, 1472,1390,1370 1315,1207,1090, 1065,1042,1030, |
| (9) | Specific rotation | $[\alpha]_D^{25°} + 350° \pm 10°$ (C = 0.5,methanol) | $[\alpha]_D^{25°} + 62° \pm 4°$ (C = 0.5,methanol) |
| (10) | Color reactions | Negative: ninhydrin reaction, | Negative: ninhydrin reac- |

TABLE 4-continued

| | C-14919 E-1 | C-14919 E-2 |
|---|---|---|
| | Ehrlich reaction, Peptide reaction, magnesium acetate reagent and 1% iron chloride-1% ferricyanide(1:1) reagent<br><br>Pottasium permanganate reagent, discolored | tion,Ehrlich reaction,peptide reaction and magnesium acetate reagent<br><br>Positive:<br>1% iron chloride −1% ferricyanide (1:1) reagent (blue)<br><br>Potassium permanganate reagent, discolored |

| | | $\delta$(ppm) | J(Hz) | Number of protons | $\delta$(ppm) | J(Hz) | Number of protons |
|---|---|---|---|---|---|---|---|
| 11 | Nuclear magnetic resonance spectrum (100 megacycles) in dimethylsulfoxide | 0.63 | d  6.5 | 3H | 0.63 | d  7 | 3H |
| | | 0.94 | d  6.5 | 3H | 0.82 | d  7 | 3H |
| | | 0.96 | d  6.5 | 3H | 0.89 | d  7 | 3H |
| | | 1.4 | s | 3H | 1.16 | s | |
| | | 1.88 | s | 3H | 1.55 | m | |
| | | 1.4–1.8 | m | | 1.83 | s | 3H |
| | | 2.2–2.4 | m | | 2.1–2.2 | m | |
| | | 3.0–3.2 | m | | 2.65 | m | |
| | | 3.23 | s | 3H | 2.86 | m | |
| | | 3.27 | s | 3H | 3.13 | s | 3H |
| | | 3.43 | s | 3H | 3.24 | s | 3H |
| | | 3.3 | m | | 3.2 | m | |
| | | 4.5 | s | 1H | 3.39 | s | 3H |
| | | 5.21 | d  10 | 1H | 4.54 | d  5 | 1H |
| | | 5.28 | d | 1H | 4.64 | d  8 | 1H |
| | | 5.59 | dd  8,10 | 1H | 5.02 | d  8 | 1H |
| | | 6.22 | t  11 | 1H | 5.21 | d  10 | 1H |
| | | 6.32 | s (disappears by addition of $D_2O$) | 1H | 5.86 | t  10 | 1H |
| | | | | | 5.98 | s. like | 1H |
| | | | | | 6.23 | s (disappears by addition of $D_2O$) | 1H |
| | | 6.41 | d  2 | 1H | | | |
| | | 6.81 | d  2 | 1H | | | |
| | | 6.95 | d  11 | 1H | 6.35 | d  2.5 | 1H |
| | | 9.3 | s (disappears by addition of $D_2O$) | 1H | 6.45 | d  2.5 | 1H |
| | | | | | 7.51 | s (disappears by addition of $D_2O$) | 1H |
| | | | | | 8.64 | s  " | 1H |
| | | | | | 8.85 | s  " | 1H |
| (12) | Stability | Room temp.:<br>Stable in neutral and weakly acidic solutions;<br>Unstable in basic solution.<br>80° C., 1hr.:<br>unstable | | | Room temp.:<br>Stable under neutral and weakly acid conditions;<br>Unstable under basic conditions.<br>80° C., 1hr.:<br>unstable | | |
| (13) | Thin layer chromatography<br>Adsorbent:<br>Silica Gel, Spot Film(Tokyo Kasei)<br>Chloroform-methanol (9:1) | 0.85 | | | 0.50 | | |
| | Chloroform-methanol (19:1) | 0.77 | | | 0.22 | | |
| | Ethyl acetate-acetone (9:1) | 0.80 | | | 0.50 | | |
| | Ethyl acetate- | | | | | | |

TABLE 4-continued

|  | C-14919 E-1 | C-14919 E-2 |
|---|---|---|
| methanol (9:1) | 0.85 | 0.78 |

Antimicrobial activity

The antimicrobial activities of Antibiotics C-14919 E-1 and E-2 were assayed by the serial dilution method using Trypticase-soy agar(BBL), glucose nutrient agar and glycerol nutrient agar as test media (Table 5). In addition, the activities against Tetrahymena pyriformis W were determined by the serial dilution method using the assay medium [Proteose-peptone 20 g, yeast extract 1 g, glucose 2 g, distilled water 1000 ml, 1 M-phosphate buffer (pH 7.0) 10 ml].

TABLE 5

| Assay organisms | IFO No. | C-14919E-1 MIC(μg/ml) | C-14919E-2 MIC(μg/ml) |
|---|---|---|---|
| *Escherichia coli K-12 | 3301 | >100 | >100 |
| Proteus vulgaris | 3045 | >100 | >100 |
| Pseudomonas aeruginosa | 3080 | >100 | >100 |
| Salmonella typhimurium | 12529 | >100 | >100 |
| Alcaligenes faecalis | 13111 | >100 | 100 |
| Serratia marcescens | 3046 | >100 | >100 |
| Bacillus pumilus | 3813 | 50 | 100 |
| Bacillus subtilis 6633 | 3134 | 50 | 100 |
| Bacillus subtilis PCI219 | 3513 | 100 | >100 |
| Bacillus cereus | 3514 | >100 | >100 |
| Bacillus megaterium | 12108 | 50 | 50 |
| Bacillus brevis | 3331 | 50 | 50 |
| Staphylococcus aureus 209P | 12732 | >100 | >100 |
| Sarcina lutea | 3232 | 50 | 50 |
| Micrococcus flavus | 3242 | 50 | 50 |
| Candida albicans | 0583 | 25 | 6.25 |
| **Candida tropicalis | 1400 | >100 | >100 |
| Candida pseudotropicalis | 0617 | 100 | 100 |
| Candida utilis | 0619 | >100 | >100 |
| Candida parapsilosis | 1396 | 50 | 25 |
| Candida krusei | 1395 | >100 | >100 |
| Candida albicans | 0583 | 50 | 25 |
| Cryptococcus neoformans | 0410 | >100 | >100 |
| Saccharomyces cerevisiae | 0209 | 100 | 100 |
| Micrsporum canis | 7863 | >100 | >100 |
| Microsporum cookei | 8303 | >100 | >100 |
| Aspergillus niger | 4066 | 100 | 100 |
| Trychophyton rubrum | 5467 | >100 | >100 |
| Hormodendrum pedrosoi | 6071 | >100 | >100 |
| Penicillium chrysogenum | 4626 | 50 | 25 |
| ***Mycobacterium avium |  | >100 | >100 |
| Mycobacterium phlei |  | >100 | >100 |
| ****Tetrahymena pyriformis W W |  | 10 | 10 |

Note: Medium
*Trypticase-soy agar
**Glucose nutrient agar
***Glycerol nutrient agar
**** Proteose-peptone solution

Toxicity

The assumed $LD_{50}$ as determined by intraperitoneal administration of C-14919 E-1 and E-2 in an acute toxicity test using mice as test animals are as follows.

| C-14919 E-1 | 50–100 mg/kg |
|---|---|
| C-14919 E-2 | 25–100 mg/kg |

As will be seen from the antimicrobial spectrum of Table 5, C-14919 E-1 & E-2 display activity against Gram-positive bacteria, fungi and yeasts. Therefore, the antibiotics are of use as germicides or disinfectants against pathogenic bacteria or fungi of the samespecies as the assay organisms.

Antitumour activity

The thereapeutic activity (intraperitoneally administered for a consecutive days) of C-14919 E-1 and E-2 against P388 leukemia in mice ($1 \times 10^6$ cells/animals, mouse, itraperitoneally transplanted) was investigated. The antitumour activity in terms of the extension of life spans was 144% at the dose level of 5 mg/kg/day.

Thus, since Antibiotics C-14919 E-1 and E-2 have a life-extending effect upon tumour-bearing mammals (e.g. mouse), they are expected to be useful as antitumour agents.

By formulating the present Antibiotic C-14919 E-1 or E-2 into an aqueous solution containing 10 to 100 μg/ml of aqueous ethnaol (e.g. containing 5% ethanol), it can be used for the disinfection of bird cages, laboratory equipment, human hands, etc.

The following examples are further illustrative but by no means limitative of the invention, wherein "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

Strain No. C-14919 (ATCC 31280, IFO 13723; FERM 3991) was inoculated on the tyrosine agar medium, followed by incubation at 28° C. for 240 hours. The well-grown mycelium was suspended in a 0.6% solution of sodium glutamate and stored in a refrigerator. A 1 part by volume-portion of the mycelial suspension was used to inoculate a 2000 parts by volume fermenter containing 500 parts by volume of a seed culture medium (20 parts of glucose, 30 parts of soluble starch, 10 parts of corn steep liquor, 10parts of soybean flour, 5 parts of peptone, 3 parts of sodium chloride and 5 parts of calcium carbonate/water 1000 parts by volume, pH 7.0). The inoculated medium was incubated on a reciprocating shaker at 28° C. for 48 hours. This culture (500 parts by volume) was used to inoculate a 50000 parts by volume tank of stainless steel charged with 30000 parts by volume of a seed culture medium. This seed culture was carried out under the following conditions: 28° C., 30000 parts by volume/min. aeration, 280 r.p.m. (½ DT), internal pressure 1 kg/cm², 48 hrs. A 10,000 parts by volume portion of the resultant preculture was used to seed a 200,000 parts by volume tank of stainless tank charged with 100,000 parts by volume of a fermentation medium (5% of glycerol, 2% of corn steel liquor, 2% of yeast extract, 2% of $KH_2PO_4$, 0.5% of $MgCl_2$ and 0.1% of $CaCO_3$, pH 6.5) and sterilized. The initial phase of fermentation was carried out under the following conditions: temperature 28° C., 100,000 parts by volume/min. aeration, 180 r.p.m. (½ DT), internal pressure 1 kg/cm², 24 hours, whereby the microorganism was allowed to grow well. Thereafter, the cultivation was further carried out for 114 hours under the same conditions as above except that the incubation temperature was 24° C. and the stirring was effected at 200 r.p.m. (½

DT). At the end of the above period, the mycelia were separated from the filtrate by filtration. The filtrate contained 380 µg/ml of activity, while the titer in the mycelia was 90 µg/cells in one part of broth. The potency titrations were carried out by the cylinder method or the paper disc method using *Candida albicans* IFO 0583 as an assay organism and C-14919 E-1 as a standard test material.

EXAMPLE 2

The procedures described in Example 1 were duplicated up to the seed culture stage. Then, the cultivation was carried out in a 200,000 parts by volume tank of stainless steel charged with 100,000 parts by volume of a fermentation medium (5% of mannitol, 3% of dried yeast, 0.5% of $MgCl_2$ and 0.1% of $CaCO_3$, pH 6.5) and sterilized. The initial phase of cultivation was conducted at 26° C., 100,000 parts by volume/min. aeration, 180 r.p.m. ($\frac{1}{2}$ DT) and internal pressure 1 $kg/cm^2$ for 18 hours. Thereafter, the cultivation was further continued for 106 hours at 24° C. and 200 r.p.m. ($\frac{1}{2}$ DT) and under otherwise the same conditions as above. At the end of the above cultivation time, the activity of the filtrate was 310 µg/ml and that of the cells was 100 µg/cells in 1 ml of broth.

EXAMPLE 3

The culture broth obtained in Example 1 (95000 parts by volume) was admixed well with 2000 parts of Hyflo-Supercel (Johnes Manville Products, U.S.A.). The mixture filtered on a filter press to obtain 85,000 parts by volume of filtrate and 31,000 parts of moist cells. The filtrate (85,000 parts by volume) was extracted with 30,000 parts by volume of ethyl acetate under stirring and their procedure was repeated twice. The ethyl acetate layers were pooled, washed twice with 30,000 parts by volume portions of water, dried by the addition of 500 parts of anhydrous sodium sulfate and concentrated to 200 parts by volume under reduced pressure. The concentrate was allowed to stand in the cold room and the crude crystals of C-14919 E-2 were recovered by filtration (8.2 parts). The filtrate was further concentrated to 50 parts by volume, followed by addition of 300 parts by volume of petroleum ether. The resultant precipitate was recovered by filtration. The resultant crude crystals (38 parts) were dissolved in 50 parts by volume of methanol and after the addition of 5 parts of silica gel (Merck, West Germany, 0.05–0.2 mm), the methanol was distilled off under reduced pressure. The residue was put onto the top of a column of 500 parts by volume silica gel (same as above). The column was washed with 500 parts by volume of hexane and elution was carried out with 1,000 parts by volume of hexane-ethyl acetate (1:1), 1000 parts by volume of ethyl acetate and 1000 parts by volume of ethyl acetate-methanol (30:1), the elute being collected in 100 parts by volume fractions. C-14919 E-1 was eluted from the column in fractions No. 13 to No. 16, while C-14919 E-2 was eluted in fractions No. 21 to No. 23. The C-14919 E-1 fractions (400 parts by volume) were pooled and concentrated and, after the addition of 80% aqueous methanol, allowed to stand in the cold room. The resultant crystals were collected by filtration. This procedure yielded 10 parts crystals. The C-14919 E-2 (300 parts by volume) were also pooled, concentrated to 100 parts by volume and allowed to stand in the cold room. The crystals were recovered and dried. By this procedure was obtained a 6.8 parts crop of C-14919 E-2 crystals.

Separately, 31,000 parts of the moist cells were extracted twice with 40,000 parts by volume portions of 70% acetone water and the resultant extracts are pooled and concentrated under reduced pressure to remove the acetone. The aqueous extract was diluted with water to 30,000 parts by volume and passed through a prepared column of 1,000 parts by volume Diaion HP-10 (Mitsubishi Kasei), whereby the active component was adsorbed. The column was washed with 2,000 parts by volume of water and 2,000 parts by volume of 40% methanol-water in the order mentioned, followed by elution with 2,500 parts by volume of 60% methanol-water and 2,500 parts by volume of 90% methanol-water in that order. The eluate was collected in 250 parts by volume fractions and the fractions Nos. 3 and 4 were combined, concentrated under reduced pressure and allowed to stand in the cold room. The resultant crude crystals of C-14919 E-2 were collected by filtration and dried (1.8 parts). The fractions Nos. 13, 14 and 15 were pooled, concentrated under reduced pressure and, after the addition of 80% methanol-water, allowed to stand in the cold room. The resultant crude crystals of C-14919 E-1 were collected by filtration and dried (5.8 parts).

EXAMPLE 4

The filtrate obtained in Example 3 (85,000 parts by volume) was extracted twice with 30,000 parts by volume portions of ethyl acetate as in Example 3 and the ethyl acetate layers were pooled, washed with 30,000 parts by volume of water and concentrated under reduced pressure down to 500 parts by volume. To the concentrate was added 4,000 parts by volume of methanol, followed by addition of 4,000 parts by volume of water and 3,000 parts by volume of hexane. After stirring, the bottom layer was separated. To the bottom layer was added a solution of 20 parts ferric chloride in 8,000 parts by volume of water, and with occasional stirring, the mixture was allowed to stand at room temperature for 5 hours, at the end of which time it was cooled. The resultant crude crystals of C-14919 E-1 were collected by filtration and dried (18 parts). The filtrate was further extracted with 5,000 parts by volume of ethyl acetate. The ethyl acetate solution was washed with water and concentrated. Upon addition of petroleum ether to the concentrate 13 parts of crude powders of C-14919 E-1 were obtained. As in Example 3, the crude powders were chromatographed on a column (200 parts by volume) of silica gel (Merck, West Germany, 0.05 to 0.2 mm) using the solvents mentioned. By the above procedure was obtained 7.2 parts of crude C-14919 E-1 crystals.

EXAMPLE 5

The C-14919 E-1 crystals (0.400 part) obtained in Examples 3 and 4 were dissolved in 40 parts by volume of ethyl acetate and, in a separatory funnel of 100 parts by volume capacity, 30 parts by volume of water was added. Then, with 0.500 part of sodium hydrosulfite ($Na_2S_2O_4$), the solution was shaken intensively. The mixture was allowed to stand and the bottom layer was discarded. Then, the upper layer was shaken well with 30 parts by volume of water and 0.500 part of sodium hydrosulfite ($Na_2S_2O_4$). The bottom layer was discarded and the ethyl acetate layer was washed well with water and dried by the addition of anhydrous sodium sulfate. After drying, the ethyl acetate layer was concentrated to dryness under reduced pressure at low temperature. The residue was dissolved by the addition of 10 parts by volume of methanol and filtered. Following the addition of 40 parts by volume of water, the filtrate was allowed to stand in the cold room. The resultant C-14919 E-2 crystals were collected by filtration and dried. m.p. 147°–148° C. (decomp.)

EXAMPLE 6

The C-14919 E-2 crystals (0.400 part) obtained in Example 3 were dissolved in 60 parts by volume of methanol, followed by addition of 32 parts by volume of a 1% aqueous solution of ferric chloride. The mixture was allowed to stand at room temperature for 1 hour and the resultant C-14919 E-1 crystals were collected by filtration, washed with 20% methanol-water and dried. m.p. 186°–187° C. (decomp.)

EXAMPLE 7

The crude crystals of C-14919 E-1 (4 parts) obtained according to Example 3 were dissolved in 600 parts by volume of methanol and, after filtering, 200 parts by volume of water was added. The mixture was allowed to stand in the cold room and the resultant purified crystals of C-14919 E-1 were collected by filtration and dried (2.8 parts). m.p. 187°–188° C. (decomp.)

Similarly, 3.5 parts of the crude C-14919 E-2 crystals obtained by the procedure of Example 3 were dissolved in 100 parts by volume of methanol and, after filtering, 500 parts by volume of water was added. The mixture was cooled and the resultant purified crystals of C-14919 E-2 were collected by filtration (2.1 parts). m.p. 148° C. (decomp.)

Figure 1:
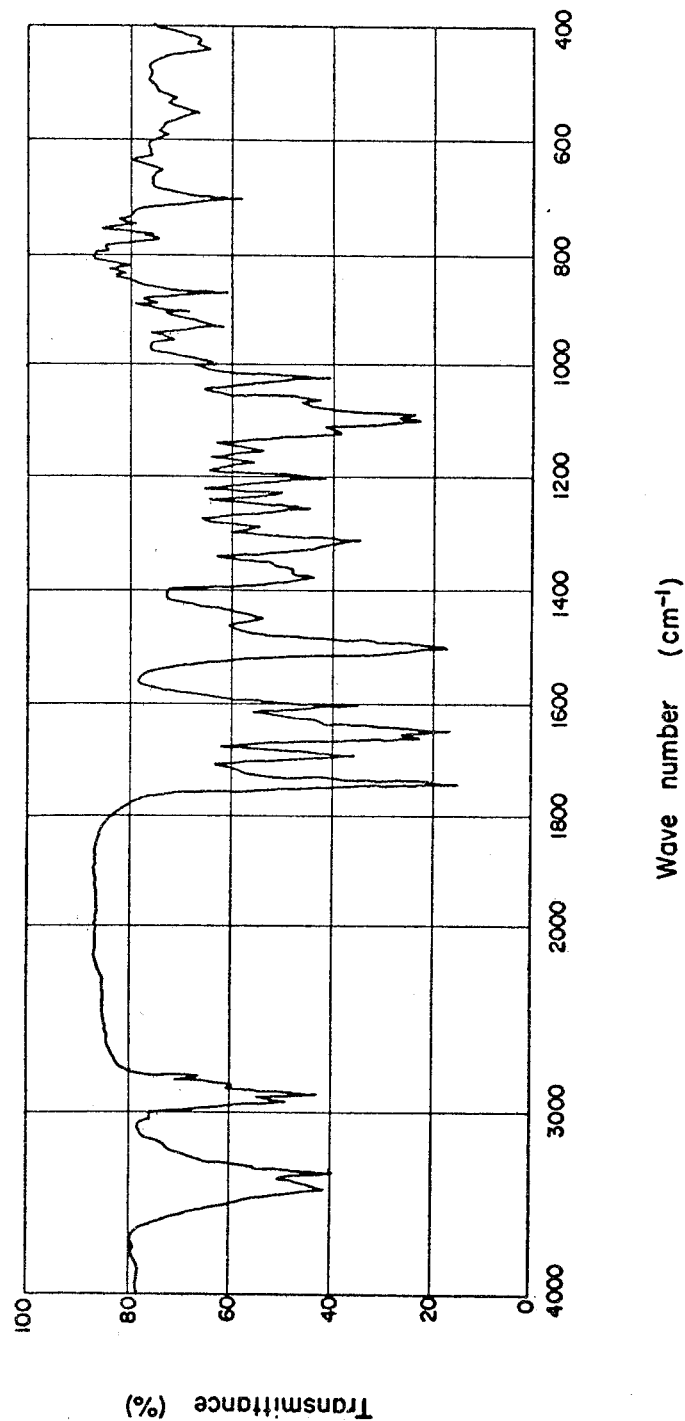
FIG. 1 is an infrared absorption spectrum of Antibiotic C-14919 E-1 in KBr.
Figure 2:
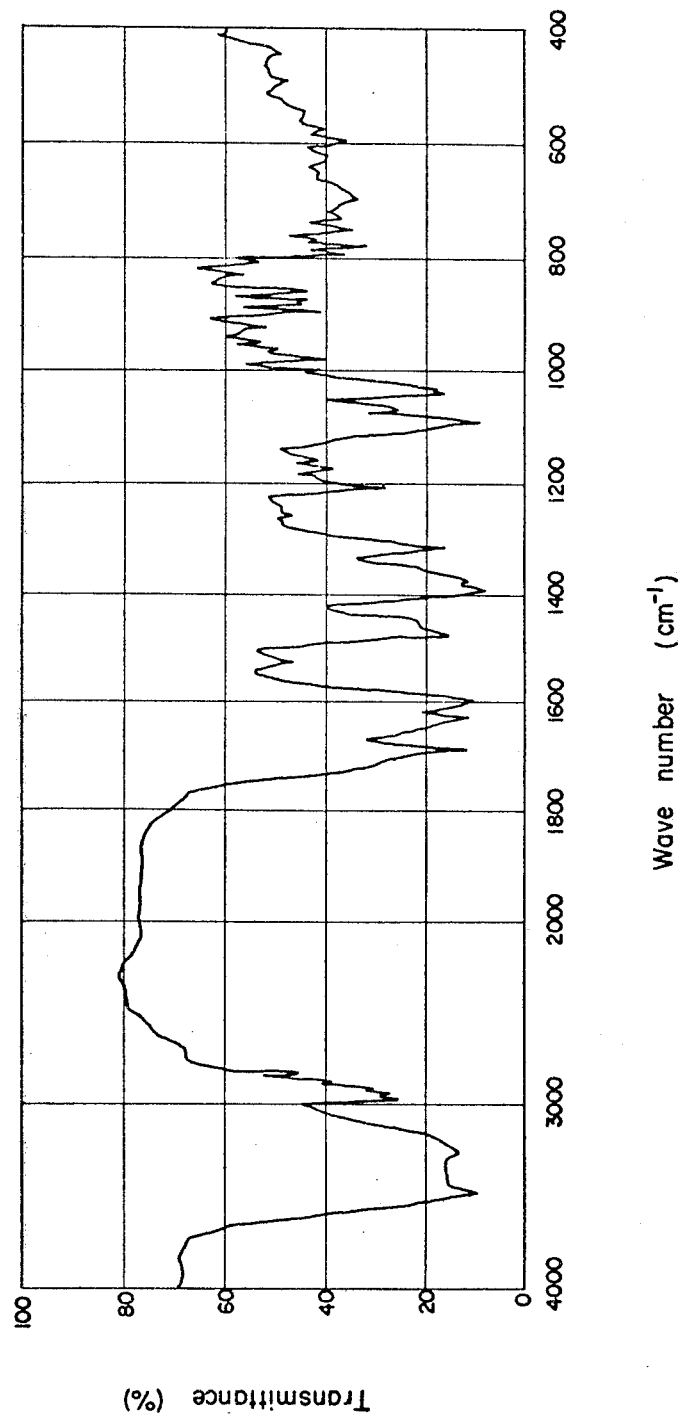
FIG. 2 is an infrared absorption spectrum of Antibiotic C-14919 E-2 in KBr.

What we claim is:

1. A method of producing Antibiotic C-14919 E-1 and/or E-2 having the following characteristics:

(a) Antibiotic C-14919 E-1
(i) m.p. 187° C. (decomp.)
(ii) Appearance: yellow crystals (needles or prisms)
(iii) Solubility:
Insoluble in: petroleum ether, hexane, water
Sparingly soluble in: diethyl ether, benzene
Soluble in: ethylacetate, chloroform, butanol, methyl isobutyl ketone, ethanol, acetone, methanol
Readily soluble in: dimethylsulfoxide
(iv) Acid, neutral or basic: a neutral substance
(v) elemental analysis:
C, 65.31; 65.05; 64.85 (%)
H, 7.71; 7.58; 7.62
N, 5.01, 4.95, 5.01
O, 21.37; 22.83; 22.45
(vi) Empirical formula: $C_{30-32}H_{42-48}N_2O_{8-9}$
(vii) Ultraviolet absorption spectrum:
$\lambda_{max}$MeOH: N-HCl(9:1) (nm) ($E_1^{1\%}{}_{cm}$):274(455), 240(sh.), 397(43)
$\lambda_{max}$MeOH(nm) ($E_1^{1\%}{}_{cm}$): 274(455), 240(sh.), 397(43)
$\lambda_{max}$MeOH: N-naOH(9:1) (nm) ($E_1^{1\%}{}_{cm}$): 236(585), 265(500), 550(56)
(viii) Infrared absorption spectrum (KBr):
Dominant peaks ($cm^{-1}$) at:
3430, 3340, 2950, 2910, 1740, 1692, 1660, 1645, 1605, 1500, 1375, 1315, 1120, 1100, 1085, 1060, 1025
(ix) Specific rotation: $(\alpha)_D^{25°} + 350° \pm 10°$ (c=0.5, methanol)
(x) Color reactions
Negative ninhydin, Ehrlich, peptide and 1% iron chloride-1% ferricyanide (1:1) reactions
(b) Antibiotic C-14919 E-2
(i) m.p. 148° C. (decomp.)
Positive 1% iron chloride-1% ferricyanide (1:1) reaction (blue) characterized in that said method comprises cultivating an Antibiotic C-14919 E-1 and/or E-2 producing strain of the genus Nocardia in a culture medium to cause said strain to elaborate and accumulate a sufficient amount of Antibiotic C-14919 E-1 and/or E-2 in the resultant broth and harvesting said Antibiotic C-14919 E-1 and/or E-2 from the cultured broth.

2. A method as claimed in claim 1, wherein the microorganism in Nocardia No. C-14919 (ATCC 31280; IFO 13723; FERM 3991) or its mutants or variants.

* * * * *

UNITED STATES PATENT AND TRADEMARK OFFICE
CERTIFICATE OF CORRECTION

PATENT NO. : 4,245,047
DATED : January 13, 1981
INVENTOR(S) : Eiji HIGASHIDE; Mitsuko ASAI; Toru HASEGAWA It is certified that error appears in the above-identified patent and that said Letters Patent are hereby corrected as shown below:

In Col. 16, between lines 32 and 33, i.e., between the expressions "(i) m.p. 148°C (decomp.)" and "Positive 1% iron chloride -1% ferricyanide (1:1)", add the following description:

-- (ii) Appearance: Pale yellow crystals (needles or prisms)

(iii) Solubility:

Insoluble in: petroleum ether, hexane

Sparingly soluble in: diethyl ether, benzene, chloroform, water

Soluble in: ethyl acetate, butanol, methyl isobutyl ketone, ethanol, acetone, methanol Readily soluble in: dimethylsulfoxide (iv) Acid, neutral or basic: a neutral substance (v) Elemental analysis:

C, 62.32; 62.07 (%)

H, 8.58; 8.43

N, 4.82; 4.78

O, 20.81: 20.81

(vi) Empirical formula: $C_{30-32}H_{44-50}N_2O_{8-9} \cdot xH_2O$

UNITED STATES PATENT AND TRADEMARK OFFICE
CERTIFICATE OF CORRECTION

PATENT NO. : 4,245,047

DATED : January 13, 1981

INVENTOR(S) : Eiji HIGASHIDE; Mitsuko ASAI; Toru HASEGAWA

It is certified that error appears in the above-identified patent and that said Letters Patent are hereby corrected as shown below:

(vii) Ultraviolet absorption spectrum:

$\lambda_{max}^{MeOH:\ \underline{N}-HCl\ (9:1)}(nm)\ (E_{1\ cm}^{1\%})$: 255(295), 308 (sh.)

$\lambda_{max}^{MeOH}(nm)\ (E_{1\ cm}^{1\%})$: 255(290), 308(sh.)

$\lambda_{max}^{MeOH:\ \underline{N}-NaOH}(nm)\ (E_{1\ cm}^{1\%})$: 236(505), 265(420), 550(50)

(viii) Infrared absorption spectrum (KBr):

Dominant peaks ($cm^{-1}$) at:

3480, 3250, 2980, 1685, 1625, 1598, 1472, 1390, 1370, 1315, 1207, 1090, 1065, 1042, 1030

UNITED STATES PATENT AND TRADEMARK OFFICE
CERTIFICATE OF CORRECTION

PATENT NO. : 4,245,047
DATED : January 13, 1981
INVENTOR(S) : Eiji HIGASHIDE; Mitsuko ASAI; Toru HASEGAWA It is certified that error appears in the above-identified patent and that said Letters Patent are hereby corrected as shown below:

(ix) Specific rotation: $[\alpha]_D^{25°} + 62° \pm 4°$ (c=0.5, methanol)

(x) Color reactions

Negative ninhydrin, Ehrlich and peptide reactions; --

Signed and Sealed this

Twenty-seventh Day of October 1981

[SEAL]

Attest:

Attesting Officer

GERALD J. MOSSINGHOFF

Commissioner of Patents and Trademarks